United States Patent [19]
Pless et al.

[11] Patent Number: 5,489,293
[45] Date of Patent: Feb. 6, 1996

[54] METHOD AND APPARATUS FOR TREATING CARDIAC TACHYARRHYTHMIA

[75] Inventors: Benjamin D. Pless, Atherton; Rose A. Province, San Francisco, both of Calif.

[73] Assignee: Ventritex, Inc., Sunnyvale, Calif.

[21] Appl. No.: 221,343

[22] Filed: Mar. 31, 1994

Related U.S. Application Data

[63] Continuation-in-part of Ser. No. 114,574, Aug. 31, 1993.

[51] Int. Cl.$^6$ .................................................. A61N 1/39
[52] U.S. Cl. ................................................................. 607/5
[58] Field of Search ........................... 607/5, 14, 15, 607/25, 26, 70, 72

[56] References Cited

U.S. PATENT DOCUMENTS

| | | |
|---|---|---|
| 4,384,585 | 5/1983 | Zipes . |
| 4,398,536 | 8/1983 | Nappholz et al. . |
| 4,574,437 | 3/1986 | Segerstad et al. ............... 607/15 |
| 4,637,397 | 1/1987 | Jones et al. . |
| 4,708,145 | 11/1987 | Tacker, Jr. et al. . |
| 4,727,877 | 3/1988 | Kallok . |
| 4,850,357 | 7/1989 | Bach, Jr. . |
| 4,941,471 | 7/1990 | Mehra . |
| 4,996,984 | 3/1991 | Sweeney . |
| 5,007,422 | 4/1991 | Pless et al. . |
| 5,107,834 | 4/1992 | Ideker et al. . |
| 5,193,536 | 3/1993 | Mehra . |
| 5,282,836 | 2/1994 | Kreyenhagen et al. .............. 607/4 |
| 5,374,279 | 12/1994 | Duffin, Jr. et al. ................. 607/5 |

FOREIGN PATENT DOCUMENTS

| | | |
|---|---|---|
| 0540266 | 5/1993 | European Pat. Off. . |
| 2141934 | 1/1985 | United Kingdom ............. 607/14 |

OTHER PUBLICATIONS

Spurrell et al., "Implantable Automatic Scanning Pacemaker for Termination of Supraventricular Tachycardia", The American Journal of Cardiology Mar. 1982, vol. 49 pp. 753–760.

"Effects of Defibrillation Shock Energy and Timing on 3–D Computer Model of Heart" Province R. A., et al., Annals of Biomedical Engineering, vol. 21, pp. 19–31 (1993).

*Primary Examiner*—William E. Kamm
*Assistant Examiner*—Jeffrey R. Jastrzab
*Attorney, Agent, or Firm*—Steven M. Mitchell; Mark J. Meltzer

[57] ABSTRACT

The present invention provides an apparatus and method for cardiac defibrillation which utilizes a lower voltage defibrillation output to depolarize the myocardial cells by providing a rapid sequence of defibrillation shocks synchronized with sensed sequential cardiac events or features during an arrhythmia. Each shock may be a conventional monophasic or biphasic pulse. Each of the shocks may be relatively short in duration, i.e. on the order of 0.5 to 3 milliseconds or may be relatively long, i.e. up to about 100 milliseconds. The amplifiers of the sensing circuitry are particularly adapted quickly recover to after each shock is delivered to allow synchronization of the next shock to the next cardiac feature. This is accomplished by using broad band amplifiers which have DC-baseline restoration capability in order to eliminate offsets caused by a preceding shock. A microprocessor in the pulse generator delivers a programmed number of pulses synchronized to the ECG. If a first sequence fails to terminate the arrhythmia, another sequence is delivered at a higher voltage and/or additional pulses are added to the sequence.

29 Claims, 6 Drawing Sheets

METHOD AND APPARATUS FOR TREATING CARDIAC TACHYARRHYTHMIA

This application is a continuation-in-part application of U.S. Ser. No. 114,574 filed Aug. 31, 1993.

FIELD OF THE INVENTION

The present invention relates generally to devices and methods for controlling cardiac arrhythmias, and more specifically to a cardioverter/defibrillator and method of delivering cardioverting and defibrillating electrical pulses to a patient's heart.

BACKGROUND OF THE INVENTION

A number of different systems and methods have been developed for delivering electrical shocks or pulses to a patient's heart for the treatment of detected abnormal rapid heart rhythms (tachyarrhythmias). These methods deliver shocks having specific waveform shapes or sequences to the heart in order to treat the detected arrhythmia by depolarizing the cardiac tissue cells. Tacker, Jr. discloses the use of sequential shocks delivered through multiple pairs of electrodes in U.S. Pat. No. 4,708,145. In Tacker, Jr., a series of rectangular or truncated exponential shocks are delivered to the heart using at least three epicardial electrodes. A first shock is sent through a first pair of the three electrodes and then a second shock is sent through a second, different pair of the electrodes. These shocks are delivered with a time separation of between 0.1 and 2 milliseconds with the preferred separation being 0.5 milliseconds. The purpose of the sequential shocks is to reduce the overall energy delivery requirements for defibrillation. A similar system using endocardial and/or subcutaneous electrodes is described in U.S. Pat. No. 4,727,877 to Kallok.

The use of two successive defibrillation pulses spaced apart by about 70 to 100 milliseconds is discussed by Province, et al. in "Effects of Defibrillation Shock Energy and Timing on 3-D Computer Model of Heart", *Annals of Biomed. Eng.*, vol. 21, pp. 19–31, 1993. In each case, a predetermined delay time is used between the first pulse and the second pulse.

The use of shocks having multiphasic waveforms is described in Jones et al., U.S. Pat. No. 4,637,397. A triphasic shock waveform is disclosed which has three pulses of alternating positive and negative polarity. U.S. Pat. No. 4,850,357 to Bach, Jr. describes the use of biphasic waveforms to defibrillate the heart. Both Jones et al. and Bach, Jr. deliver the initial portion of the shocks simultaneous with the peak of a cardiac complex.

Defibrillation shocks of the type described above are typically in the range of from about 200 to 800 volts delivered as a capacitive discharge from a source capacitance of about 100 to 150 microfarads for a time of from about 2 to 12 milliseconds. Overall energy delivery to the heart for a defibrillation shocks may typically be from about 5 to 40 joules. A monophasic defibrillation shock may typically be a truncated exponential decay with an initial voltage of about 700 volts and a duration of about 6 to 8 milliseconds. A biphasic defibrillation shock may typically have an initial positive phase of about 700 volts for a duration of 6 milliseconds and a negative phase of about 100 to 200 volts for an equal duration. The leading edge voltage of the second phase of a biphasic shock is typically equal to or one half of the trailing edge voltage of the initial phase which itself depends on the tilt of the pulse. The overall energy delivered is a function of the initial voltage, duration, source capacitance and lead impedance.

A pathological tachycardia is one form of tachyarrhythmia which is characterized by rapid but organized heart rhythms. It typically has a rate from about 110 beats per minute (bpm) to about 190 bpm, depending on the patient, and may be treated with cardioversion pulses. These shocks are similar to defibrillation shocks but generally are delivered at lower voltages, and are delivered simultaneously with the QRS complex. A single shock is delivered simultaneous with the QRS complex to help avoid accelerating a heart experiencing a ventricular tachycardia into ventricular fibrillation. Such a cardioverter is disclosed in U.S. Pat. No. 4,384,585 to Zipes. In Zipes, an implantable intracardiac cardioverter detects intrinsic depolarization of cardiac tissue and provides a single shock to the heart simultaneously with the detected cardiac activity at a time when the bulk of cardiac tissue is already depolarized and in a refractory state. According to Zipes, this reduces the energy needed for cardioversion.

Another technique for treating a pathological tachycardia is to deliver a sequence of from about three to fifteen antitachycardia pacing pulses. The first pulse in the sequence is delivered simultaneous with the R-wave of a QRS complex and the subsequent pulses are delivered with a predetermined spacing between the pulses which may be constant within a given sequence or may vary. Such a system is disclosed in U.S. Pat. No. 4,398,536 to Nappholz et al.

In European Patent Application No. 0 540 266 A1, Kroll et al. disclose a system for delivering one or more pretreatment shocks to a fibrillating heart. They explain that such pulses begin the process of organizing the action of the chaotically contracting myocardial cells so that the defibrillating shock applied after the pretreatment can accomplish its task with less energy than would otherwise be required. The pretreatment may include a train of shocks of appreciably lower energy than the defibrillation shock with various predetermined inter-pulse times. In one disclosed embodiment, a train of short duration, high voltage pretreatment shocks are followed by a high voltage defibrillation shock. The spacing between each of the pretreatment shocks and also the defibrillation shock is set at 200 milliseconds. This spacing is selected because it corresponds to a heart rate of 300 beats per minute and because it allows sufficient time for recharging of the high voltage capacitor after each shock.

In U.S. Pat. No. 5,282,836 to Kreyenhagen et al., an implantable atrial defibrillator is disclosed which provides pre-cardioversion pacing to stabilize the cardiac rate of the heart prior to the application of the cardioverting electrical energy. The rate for the stabilizing pacing is determined by averaging a last preselected number of cardiac cycles. In one embodiment, if an early ventricular activation is detected, the pacing rate is redetermined based on the more recent cardiac cycles. Typically, eight pacing pulses are delivered to the ventricle prior to delivering a cardioverting shock to the atrium.

Some prior art defibrillators deliver defibrillation shocks to the heart without any correlation or synchronization to the timing of the sensed QRS complex from an electrocardiogram (ECG). Other prior art devices synchronize such shocks to the QRS complex.

A technique for delivering a sequence of defibrillating pulses which are in-phase with the sensed ECG signal is described in U.S. application Ser. No. 114,574 filed Aug. 31, 1993 which is the parent of the present application. The ECG is continuously sensed during the application of the defibrillating output and each output is held constant until a threshold crossing of the ECG is detected, whereupon the defibrillating output is changed.

A primary goal in treating a detected tachyarrhythmia with an implantable cardioverter/defibrillator is to ensure delivery of effective therapy while minimizing energy delivery requirements for defibrillation or cardioversion. Lower voltage therapy is less painful and disruptive to the patient. Also, lower voltage electrical pulses allow for use of smaller batteries and capacitors even where the overall energy delivery is not reduced. Smaller batteries and capacitors result in a smaller implantable defibrillator and thus improved patient comfort.

SUMMARY OF THE INVENTION

The present invention provides an apparatus and method for cardiac defibrillation which utilizes a lower voltage defibrillation output to depolarize the myocardial cells by providing a rapid sequence of defibrillation shocks synchronized with sensed sequential cardiac or electrogram events or features during an arrhythmia. For purposes of this application, synchronous or synchronized is used to mean having a defined time relation. Thus, a synchronous shock may be simultaneous with a sensed feature or event or have a predetermined time delay of from about 1 to several hundred milliseconds. The sensed feature may be a threshold crossing of the ECG or may be based on the slope of the waveform. Each shock may be a conventional monophasic or biphasic shock or other known waveform. The shocks may be relatively short in duration, i.e. on the order of 0.5 to 3 milliseconds or may be relatively long, i.e. up to about 100 milliseconds, or somewhere between. After each shock is delivered, the amplifiers of the sensing circuitry are caused to quickly recover. This is accomplished by using broad band amplifiers which have DC-baseline restoration capability in order to eliminate offsets. A microprocessor in the pulse generator delivers a programmed number of pulses synchronized to the ECG. If a first sequence fails to terminate the arrhythmia, another sequence is delivered at a higher voltage and/or additional pulses are added to the sequence. In some cases, some of the pulses may be delivered asynchronously without significantly degrading the efficacy of the treatment.

Conventional techniques are used to identify the presence of an arrhythmia, typically based on measured intervals between cardiac complexes. A synchronization trigger is generated from a feature of the sensed ECG signal and may be derived from a threshold crossing of the signal such as with a s positive or negative peak or by monitoring the slope of the signal for a high or low rate of change of the voltage.

The delivered shocks may be from the discharge of a single capacitor or a capacitor stack which is charged from a battery by a power supply circuit. Alternatively, a constant current or constant voltage source may be used. Where a constant current output is used, this may be delivered from a high voltage capacitor charged before delivery of the pulse sequence. The shocks are preferably delivered through a bridge of switches to allow delivery of biphasic shock waveforms.

In an alternative embodiment of the invention, the microprocessor analyzes the intervals between successive shocks to determine when to cease shock delivery based, for example, on the interval becoming very stable.

In a further embodiment of the invention, a sequence of substantially synchronous defibrillation pulses are delivered to the patient's heart by sensing an ECG signal, detecting fibrillation, determining a fibrillation interval, and delivering in a sequence of defibrillation pulses to the patient's heart having a timing directly related to the determined fibrillation interval.

In another alternative embodiment, the system of the invention is used first to convert ventricular fibrillation to ventricular flutter or ventricular tachycardia which may then be treated using conventional therapies such as antitachycardia pacing or cardioversion pulses.

In still another embodiment of the invention, it is preferred that the first shock in a sequence is delivered at a time when the heart is most susceptible to defibrillation. This is accomplished by delivering the first shock synchronous with a relatively high amplitude peak or during a period of course or stable fibrillation.

The different embodiments of the invention may be used to treat tachycardia as well as fibrillation. Additionally, the method and apparatus of the invention may be used with an external defibrillator.

It is thus an object of the present invention to provide a method and apparatus for delivering a defibrillation shock sequence which requires lower voltage than conventional defibrillation waveforms.

It is another object of the invention to provide a method of defibrillation which delivers lower energy shocks to the heart than conventional techniques.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1:
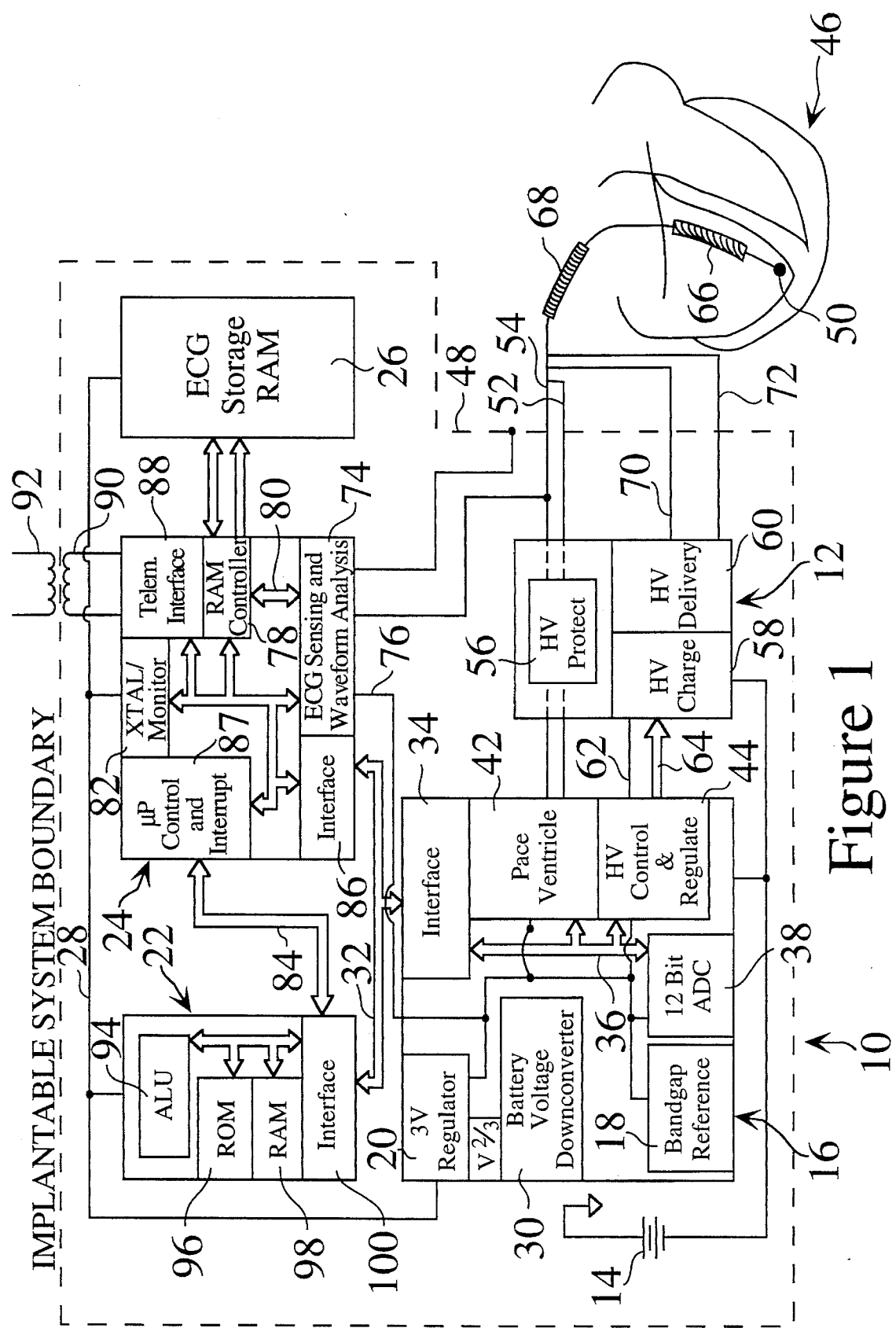
FIG. 1 is a schematic diagram of an implantable cardioverter/defibrillator of the invention.

Referring now to FIG. 1, the basic system of an implantable cardioverter/defibrillator (also referred to as a pulse generator) of the invention will be described. It should be understood that the apparatus and method of the invention, while described in connection with an implantable device, may also be implemented and used with an external defibrillator. FIG. 1 shows a block diagram of the implantable pulse generator 10 which includes four integrated circuits and a set of high voltage discretes in an output stage 12. A battery 14 produces a positive voltage with respect to ground that varies from about 6.4 volts when new, to 5.0 volts at the end of service. The battery 14 directly powers a first integrated circuit 16 and the output stage 12 which together provide for the generation and delivery of electrical shocks to the patient's heart.

Integrated circuit 16 contains a band-gap reference circuit 18 that produces an output of 1.235 volts, and a 3 volt regulator 20 that powers a microprocessor 22, a second integrated circuit 24, and an ECG storage RAM 26 through a regulated voltage supply line 28. The 3 volt regulator 20 runs off a switched capacitor V2/3 battery voltage down converter 30 for improved efficiency.

The microprocessor 22 communicates with integrated circuit 16 through a data and address bus 32 and an on-chip interface 34 that contains chip-select, address decoding and data bus logic as is typically used with microprocessor peripherals. An internal bus 36 allows the microprocessor to control a general purpose analog-to-digital converter (ADC) 38, a ventricular pace circuit 42, and a high voltage (HV) control and regulate block 44. The ADC 38 is used by the microprocessor to measure the battery and other diagnostic voltages within the device.

The ventricular pace circuit 42 includes a DAC that provides the ability to pace at regulated voltages. It communicates with the ventricle of the patient's heart 46 through a ventricular pacing/sensing lead which includes a first conductor 52 which is switchable to ground and a second conductor 54 which is connected to the pacing cathode and also serves as an input to a ventricular sense amplifier, as will be described below. Thus, the preferred embodiment for the sensing lead used in providing the synchronizing trigger is a unipolar sense signal from an endocardial pacing tip using the pulse generator housing 48, indicated as the implantable system boundary in the figure, as an indifferent electrode.

The ventricular pace lines pass through a high voltage protection circuit 56 in output stage 12 to keep the defibrillation voltages generated by the device from damaging the ventricular pace circuit 42.

The HV control and regulate block 44 on integrated circuit 16 is used by the microprocessor 22 to charge a high voltage capacitor included in an HV charge block 58, which is part of the output stage 12, to a regulated voltage and then to deliver a defibrillating pulse to the heart 46 through the action of switches in an HV delivery block 60. The output stage 12 will be discussed with reference to FIG. 2 below. In an alternative embodiment of the invention, the sequential shocks may be delivered from a constant current source or a constant voltage source.

An HV sense line 62 is used by the HV control and regulate block 44 to monitor the defibrillating voltage during charging. An HV control bus 64 is used by the HV control and regulate block 44 to control the switches in the HV delivery block 60 for delivering the defibrillating pulses to a pair of electrodes 66, 68 through a pair of high voltage delivery lines 70, 72. The preferred electrode configuration is a pair of endocardial electrodes, one electrode 66 placed in the right ventricle (RV) of the heart 46 and the other electrode 68 in the region of the superior vena cava (SVC). Alternatively, epicardial patch electrodes may be used. However, the implantation of epicardial electrodes typically involves more serious surgery and thus may be less desirable. An additional electrode such as a subcutaneous patch electrode or the pulse generator housing 48 can also be used, if needed. Alternatively, the SVC electrode could be eliminated and the electrical pulses could be delivered between an RV electrode and the pulse generator housing where the pulse generator 10 is positioned in the pectoral region of the patient's chest.

Figure 2:
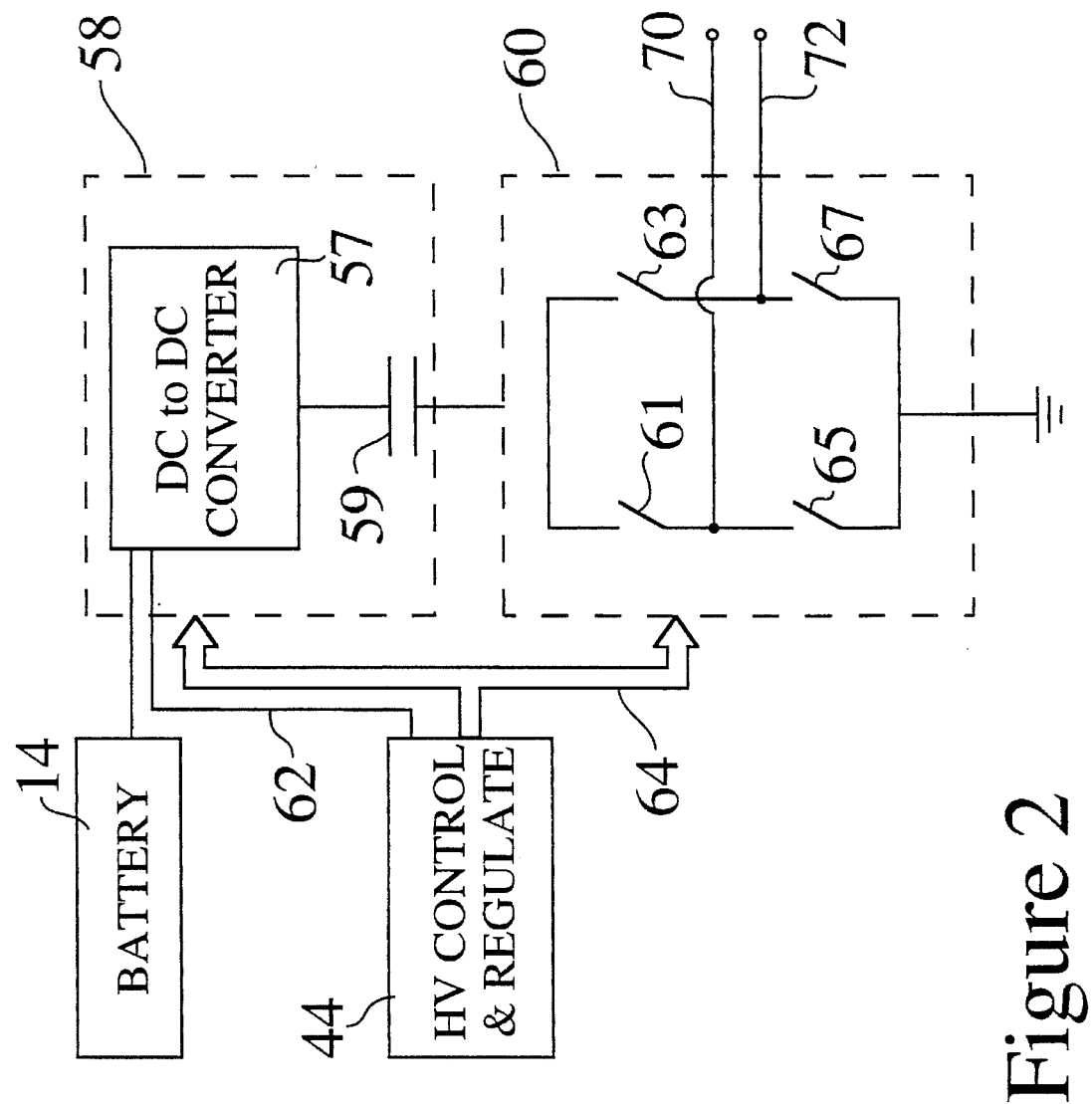
FIG. 2 is a schematic diagram of the high voltage delivery circuitry of the invention.

The output stage will now be discussed with reference to FIG. 2. Battery 14 directly powers HV charge block 58 which includes a DC to DC converter 57 and a high voltage capacitor 59. In the preferred embodiment, DC to DC converter 57 has an output capability of about 5 watts and capacitor 59 has a capacitance of 1200 microfarads with a voltage rating of about 130 volts. This provides a stored energy capability of 10 joules. While the capacitor value is substantially higher than conventional defibrillator HV capacitors, its lower voltage rating allows for the use of a higher energy density capacitor, thus resulting in a smaller defibrillation energy storage capacitor. A benefit of using the preferred embodiment is that the charge time is only about 2 seconds, thus providing a rapid response following detection of fibrillation. This is beneficial because it has been found that defibrillation thresholds (DFTs) are lower at the beginning of an arrhythmia.

Output stage 12 further includes a conventional four switch bridge for delivery of single or multiphasic pulses. The bridge consists of four transistors 61, 63, 65 and 67 which are preferably insulated gate bipolar junction transistors (IGBJTs). However, MOSFETs, JFETs or bipolar transistors could alternatively be used. The transistors are controlled by HV control and regulate block 44 through control bus 64. Because the transistors deliver lower voltage pulses than those in conventional defibrillators, they can be rated at about 150 volts and 2 ohms and thus have a reduced size. The desired pulses are delivered from HV capacitor 59 by selective opening and closing of the switches formed by transistors 61, 63, 65 and 67 in a known manner.

With the preferred embodiment, a rapid sequence of shocks, each having an energy of 1 joule, may be delivered to the patient's heart. Depending on the output of DC to DC converter 57 and the interval between shocks, there may not be sufficient time to recharge the HV capacitor 59 between shocks. If the capacitor is not fully recharged, the pulse widths of the shocks may be gradually increased to maintain a nearly constant energy delivery for each shock. TABLE 1 provides an example of a rapid pulse sequence (every 100 milliseconds) with a desired energy per pulse of 1 joule and recharging between pulses of 0.5 joules (5 watts for 100 milliseconds). A 50 ohm heart load impedance is assumed and monophasic pulses are used for simplicity.

TABLE 1

| SHOCK NUMBER | INITIAL VOLTAGE | FINAL VOLTAGE | PULSE WIDTH (msec) | SHOCK ENERGY (joules) |
| --- | --- | --- | --- | --- |
| 1 | 130 | 123 | 3.3 | 1 |
| 2 | 127 | 120 | 3.4 | 1 |
| 3 | 124 | 117 | 3.5 | 1 |
| 4 | 120 | 113 | 3.7 | 1 |
| 5 | 116 | 109 | 3.9 | 1 |
| 6 | 112 | 104 | 4.2 | 1 |
| 7 | 108 | 100 | 4.5 | 1 |
| 8 | 104 | 96 | 4.9 | 1 |
| 9 | 100 | 92 | 5.4 | 1 |
| 10 | 96 | 87 | 5.9 | 1 |

The pulse widths are increased either by sensing the capacitor voltage as an indicator that the desired energy has been delivered or by calculating the pulse width required for the desired energy with the current capacitor voltage, given a known heart impedance.

If biphasic shocks are used, the pulse width of the second phase should be considerably shorter than the first phase (on the order of one fifth) because the pulse has very low droop. Thus, if the second phase were not substantially shorter, the energy of the two phases would be about the same, which is not desirable.

In an alternative embodiment of the invention, a series of smaller capacitors, on the order of 100 microfarads may be used to produce the sequence of synchronous shocks. All of the capacitors are charged to their respective voltages and then discharged sequentially. If the intershock interval is not too short, the capacitors may be recharged in time for additional numbers of shocks beyond the number of capacitors to be delivered. One advantage of this embodiment is that each shock can have an arbitrary voltage level.

Referring back to FIG. 1, integrated circuit 24 is a microprocessor peripheral and provides timing, interrupt, telemetry, ECG storage, and sensing functions. An electrogram sensing and waveform analysis section 74 interfaces with the ventricle of the heart 46 through conductor 54. The preferred embodiment for sensing is unipolar sensing between a lead tip 50 and the pulse generator housing 48. The tip 50 can also be used for conventional pacing with pacing pulses delivered between the tip 50 and the RV electrode 66. Low polarization material such as titanium nitride is a preferred material for the tip.

Figure 3:
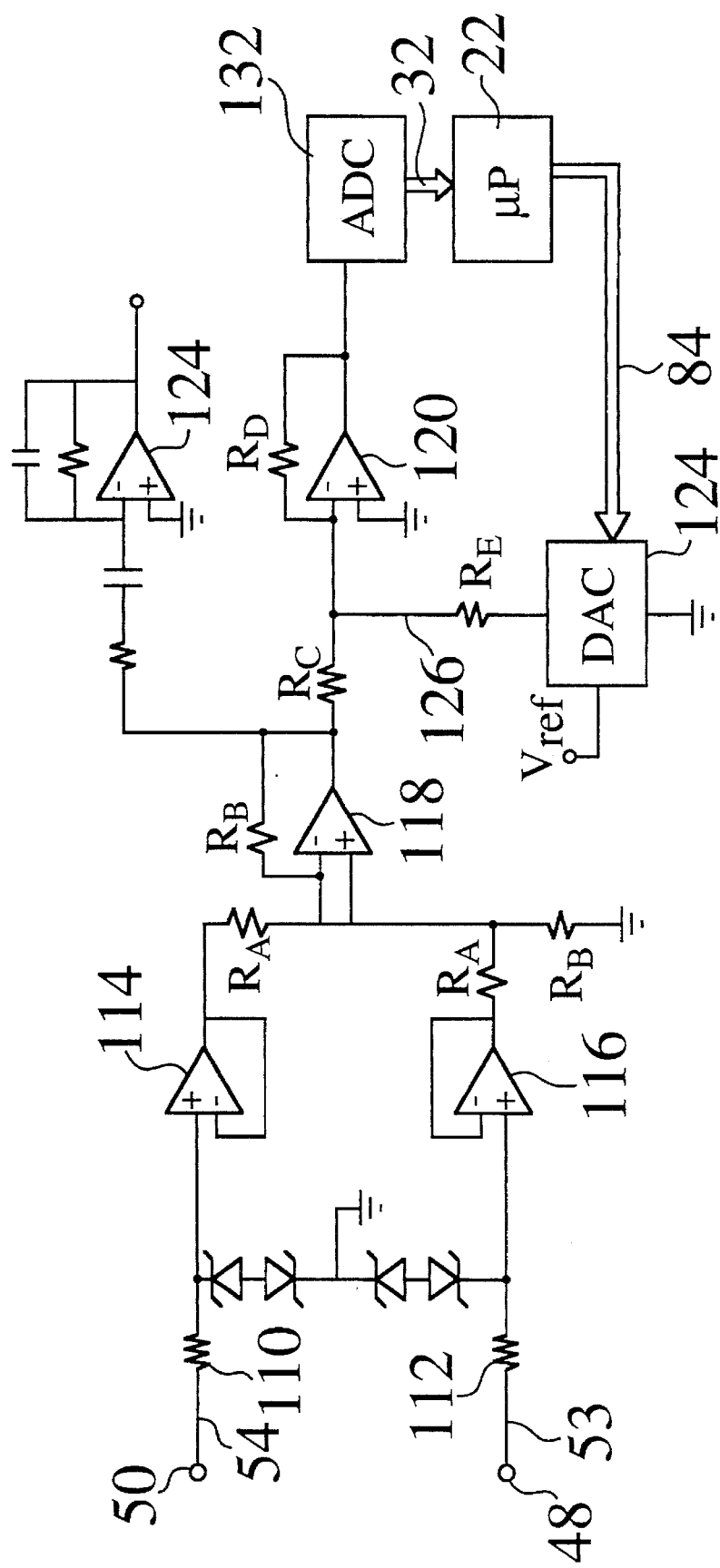
FIG. 3 is a schematic diagram of the sensing circuitry used in the preferred embodiment of the invention.

The sensed electrogram is amplified and digitized using circuitry which will be described with reference to FIG. 3. FIG. 3 is a schematic diagram of a portion of the circuitry included in electrogram sensing and waveform analysis section 74 but does not show the circuitry for waveform analysis. An electrogram is sensed between the electrode tip 50 and the pulse generator housing 48. A pair of 100 KΩ, 1 KV input resistors 112, 110 and a series of 3 volt Zener diodes 111 provide input protection for the sensing circuitry from high voltage shocks and are coupled by connectors 53, 54 to the housing 48 and tip electrode 50. A pair of high input impedance op-amps 114, 116 receive the input signal through resistors 110, 112. The outputs of the op-amps are coupled to another op-amp 118 and together this portion of the circuit provides a first stage amplifier. The output of op-amp 118 is coupled to a second stage amplifier 120 whose output is coupled to an ADC 122. ADC 122 provides the digitized electrogram to microprocessor 22 along data and address bus 32. The output of op-amp 118 is also coupled to a separate sensing amplifier 124 which provides signals in a parallel path for conventional sensing and analysis.

After a shock is delivered, the microprocessor 22 selects a baseline restoring voltage and communicates this along a control bus 84 to DAC 124. This voltage is provided by line 126 to the input of amplifier 120. Over time, the DAC 124 output is updated by the microprocessor 22 to track baseline drift or changing DC offsets.

Resistors $R_A$, $R_B$, $R_C$, and $R_D$ are selected to provide the desired signal gain for the input electrogram signal received from the heart. In the preferred embodiment, $R_B$=10 MΩ and $R_A$=200 KΩ providing a first stage signal gain of 50. The second stage gain is determined by selecting $R_D$=10 MΩ and $R_C$=300 KΩ for a gain of 20 and thus an overall signal gain of 1000. The amplifiers contained in this portion of electrogram sensing and waveform analysis section 74 may have multiple gain settings that are under microprocessor control for maintaining an automatic gain control (AGC). It is a particular feature of the invention that the sense amplifiers are broad band and use a DC-baseline restoration capability, rather than AC coupling, to eliminate offsets. This is important because sensing the next cardiac complex during fibrillation requires a recovery time of down to 80 milliseconds or so.

The amplified electrogram which is digitized using ADC 122 is analyzed by a waveform analyzer (not shown in FIG. 3). Features such as peak voltage and complex width are extracted by the waveform analysis circuits in section 74 for the microprocessor 22 to use in discriminating pathologic arrhythmias from normal sinus rhythms in a known manner. The waveform analyzer additionally provides synchronization information to microprocessor 22 which is used as described more fully below to command the HV control and regulate block 44 to deliver a sequence of synchronous pulses. A reference voltage from the 3 V regulator 20 is supplied to the DAC 124 in electrogram sensing and waveform analysis section 74 by line 76.

Referring again to FIG. 1, the digitized ECG from section 74 is provided to a RAM controller 78 through a bus 80. The RAM controller 78 sequences through the addresses of the ECG Storage RAM 26 to maintain a pretrigger area, and this produces a post trigger area upon command from the microprocessor 22.

A crystal and monitor block 82 has a 100 KHz crystal oscillator that provides clocks to the entire system. The monitor is a conventional R-C oscillator that provides a back-up clock if the crystal should fail.

The microprocessor 22 communicates with integrated circuit 24 through two buses, control bus 84 and data and address bus 32. The data and address bus 32 goes to an on-chip interface 86 on integrated circuit 24 that contains chip select, address decoding and data bus drivers as are typically used with microprocessor peripherals. Control bus 84 allows the microprocessor to set up a variety of maskable interrupts for events like timer timeouts, and sense events. If an interrupt is not masked, and the corresponding event occurs, an interrupt is sent from integrated circuit 24 to the microprocessor 22 to alert it of the occurrence. On integrated circuit 24, a microprocessor control and interrupt section 87 contains microprocessor controllable timers and interrupt logic.

The pulse generator 10 communicates with the outside world through a telemetry interface 88. A coil 90 is used in a conventional fashion to transmit and receive pulsed signals. The telemetry interface 88 decodes an incoming bit stream from an external coil 92 and holds that data for subsequent retrieval by the microprocessor 22. When used for transmitting, the interface 88 receives data from the microprocessor 22, encodes it, and provides the timing to pulse the coil 90. The communication function is used to retrieve data from the implanted device, and to change the modality of operation if required.

The microprocessor 22 is of conventional architecture comprising an Algorithmic Logic Unit (ALU) 94, a Read Only Memory (ROM) 96, a Random Access Memory (RAM) 98, and an interface circuit 100. The ROM 96 contains the program code that determines the operation of the device. The RAM 98 is used to modify the operating characteristics of the device as regards modality, pulse widths, pulse amplitudes, and so forth. Diagnostic data is also stored in the RAM for subsequent transmission to the outside world. The ALU 94 performs the logical operations directed by the program code in the ROM.

Figure 4:
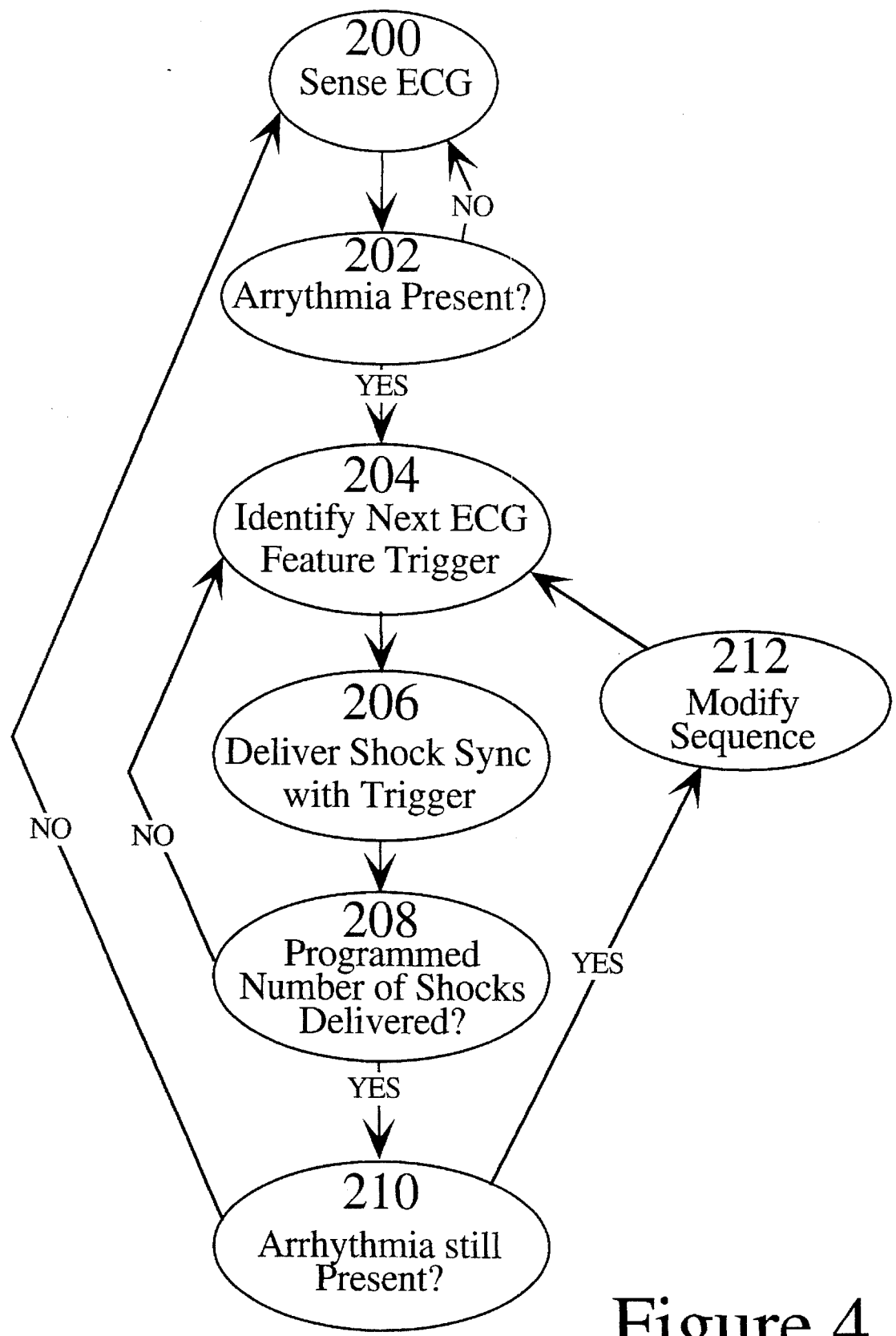
FIG. 4 is a flow diagram that illustrates a preferred method of practicing the invention.

The program code for microprocessor control of the device is written to perform certain desirable functions which are best described in flowchart form. FIG. 4 is a flow diagram that illustrates a preferred method of practicing the invention. The pulse generator continuously senses the ECG from the patient's heart at step 200 so that the device may quickly identify the presence of an arrhythmia. At step 202, the ECG is analyzed to determine whether an arrhythmia is present. A method for detecting the presence of an arrhythmia is disclosed in U.S. Pat. No. 4,971,058 to Pless et al., which patent is incorporated herein by reference in its entirety. The arrhythmia detection step 202 may include identification of a number of possible arrhythmias including fibrillation, slow rate tachycardia (TACH A) and fast rate tachycardia (TACH B). Depending on the programming of the pulse generator, a less aggressive therapy, such as antitachycardia pacing, may first be used to treat a tachycardia before the method of the invention is implemented. Once the device determines, based on its programming, that the therapy of the invention should be implemented, the steps are essentially the same for treating tachycardias and fibrillation. However, the voltage of the shocks and the number of shocks in a sequence may differ. Additionally, the waveform of the shocks, i.e. monophasic, biphasic or multiphasic, as well as the duration of each shock may differ between fibrillation treatment and tachycardia treatment. Further, the pulse width of a given waveform may be programmed or may vary as a function of the measured lead impedance. The preferred embodiment of the invention utilizes biphasic waveforms with the first phase of the waveform having a width of about 4 milliseconds and the second phase having a width of about 1 millisecond or less.

It is preferred in treating fibrillation that the first shock in a sequence be delivered at a time when the heart is most susceptible to defibrillation. This is accomplished by delivering the first shock synchronous with a relatively high amplitude peak as sensed by a far-field sensor or during a period of course or stable fibrillation. Far-field sensing may be accomplished by sensing from a pacing tip electrode to the pulse generator housing. The relatively high amplitude peak is determined by monitoring the cardiac complexes, particularly during charging of the high voltage capacitors, and setting a threshold based on the observed amplitude of these complexes, such as by a running average or a relative maximum for a window of complexes. When an average is used, the threshold is set above the average and when a relative maximum is used the threshold is set below the measured maximum. An alternative technique for determining when the heart is more susceptible to defibrillation is to look at the regularity of the fibrillation interval. It is better to shock during coarse fibrillation when the interval is more regular than during fine fibrillation.

Once the presence of an arrhythmia is detected, the waveform of the ECG is analyzed to identify a feature for use as a synchronization trigger at step 204. The trigger may be identified by a number of waveform features such as the crossing of a threshold by the electrogram signal or the slope of the waveform, i.e. the rate of change of the amplitude of the waveform with respect to time (dv/dt). The triggering slope can be either a high or low slope indicating a sharp peak or a relatively flat portion of the waveform. Other algorithms may be used to generate the synchronizing trigger. The use in the preferred embodiment of an AGC circuit and an ADC to digitize the sensed electrogram facilitates this analysis. However, the analysis could also be accomplished using analog circuitry.

A shock is delivered to the patient's heart in step 206 synchronous with the trigger determined in step 204. Certain details of these steps are discussed below in more detail with reference to FIG. 5. In the preferred embodiment, a programmed number of shocks are delivered in each sequence before a new determination is made as to whether the arrhythmia has been terminated. Each of the shocks in a sequence generally has the same amplitude. However, in an alternative embodiment, the amplitude may change from one pulse in a sequence to the next. For example, the amplitude of each subsequent shock in a sequence may decrease. The programmed number of shocks in a sequence may be anywhere from about 2 to about 15. Thus, following the delivery of each shock in a sequence, a determination is made at step 208 whether the programmed number of shocks has been delivered. If not, the control recycles to step 204 to determine the next EGG feature trigger and deliver the next shock in the sequence. The shocks in a sequence may be triggered on the same or different features of the electrogram. It should be understood that synchronous as used here does not necessarily mean simultaneous but rather means in some determined time relation. Thus, delivery of a synchronous shock may, for example, be delayed 120 milliseconds from the trigger. As previously stated, the trigger may be based on thresholds, or slopes (dv/dr) of sensed features of the electrogram.

It is preferred that each shock in a sequence be synchronous with a sensed cardiac event or feature such as a peak or return to baseline. However, the method of the invention is sufficiently robust that shocks in a sequence may be delivered asynchronously. Further, in one embodiment of the invention, a first number of shocks is delivered synchronous with sensed cardiac features or events followed by one or more extra shocks delivered at a predetermined interval(s).

In an alternative embodiment of the invention, the synchronizing algorithm can choose the phase of the output pulse. Thus, for positive electrogram deflections, a positive polarity shock is delivered and for negative polarity deflections a negative polarity shock is delivered, or vice versa. This embodiment is described below with reference to FIG. 5.

In another alternative embodiment of the invention, the sequence of shocks may be delivered with an interval which is determined based on a measured interval of the fibrillation with the first shock in the sequence being delivered synchronous with a cardiac event. In this manner, each shock may be delivered essentially synchronous with a cardiac event without having to sense the cardiac events during a sequence of shocks.

When the programmed number of shocks has been delivered, a new determination is made at step 210 as to whether an arrhythmia is present. This will typically take several seconds in order to allow a number of cardiac intervals to be detected. If the arrhythmia has been terminated and the heart returned to a sinus rhythm, the system returns to its continuous sensing mode at step 200.

If, on the other hand, an arrhythmia is still present, the system will modify the sequence parameters at step 212 for delivery of the next shock. In some instances, the arrhythmia which was being treated may have been converted to a less severe arrhythmia, such as fibrillation being converted to TACH B or TACH B being converted to TACH A. In that case, the system will revert to the particular programmed therapy for the new arrhythmia. In particular, this may involve the delivery of antitachycardia pacing therapy or it may involve delivery of a new sequence of synchronized shocks with modified sequence parameters. In other cases, the arrhythmia may not have changed. In this case, the sequence parameters may be modified to deliver a more aggressive therapy or, in some cases, the prior sequence may be repeated. Changes to the sequence parameters include increasing or decreasing the voltage of the shocks, the duration of the shocks and the number of shocks delivered. Once the new sequence parameters are defined, delivery of the next sequence is initiated at step 204.

In an alternative embodiment of the invention, an additional step may be added between step 208 and step 204 after delivery of each shock in a sequence. The interval between each shock may be monitored and if the interval is greater than a programmed threshold, indicative of a slower heart rate, the therapy may be terminated or a therapy for a less severe arrhythmia may be initiated.

Figure 5:
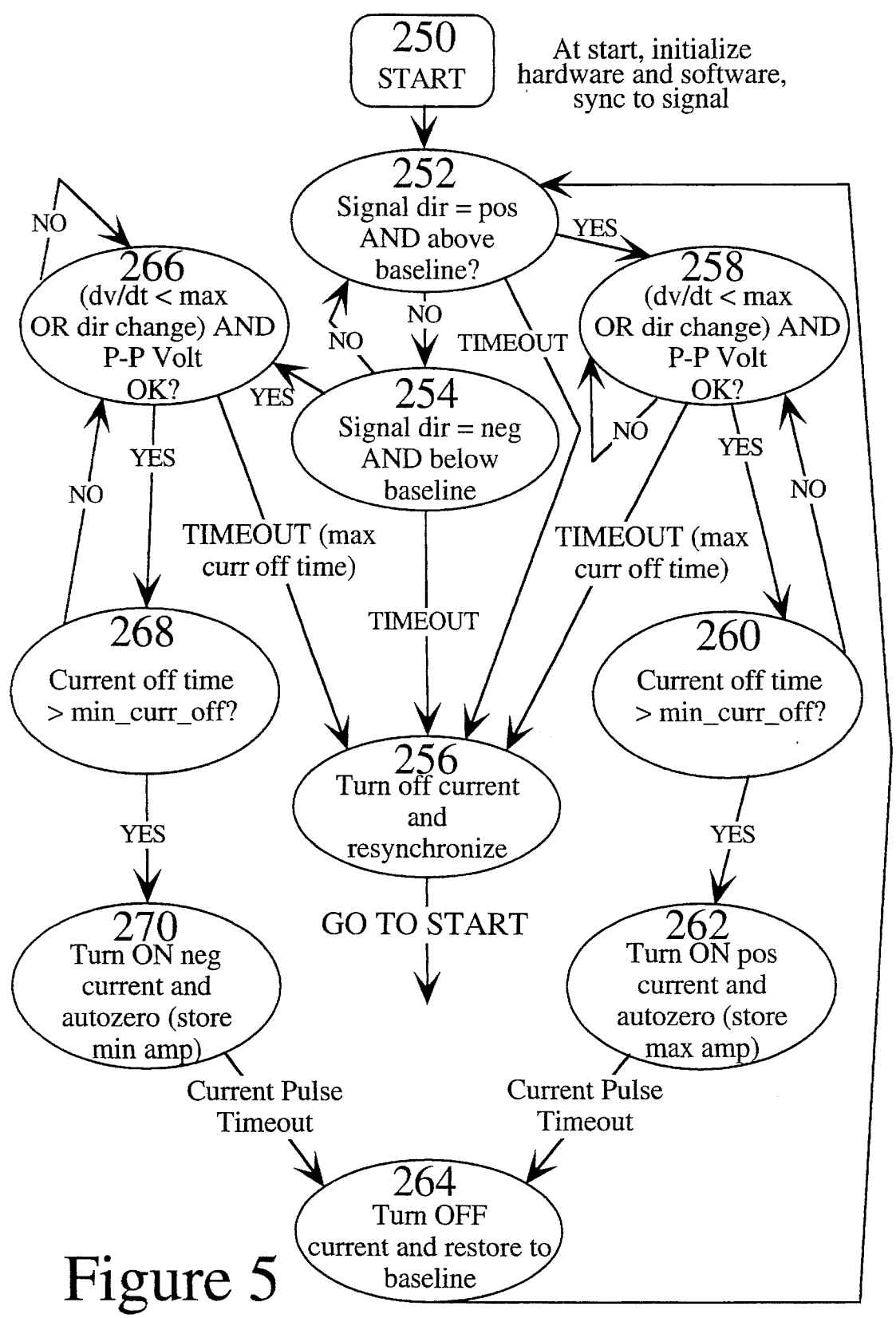
FIG. 5 is a flow diagram showing certain details of the synchronization and triggering of shocks for one embodiment of the invention.

FIG. 5 is a flow diagram showing certain details of the synchronization and triggering of shocks for one embodiment of the invention. In particular, for this illustrative embodiment, positive current shocks are delivered synchronous with positive voltage peaks and negative current shocks are delivered synchronous with negative voltage peaks. Further, each shock is delivered for a predetermined duration. The shocks are triggered by the sensed waveform having a low slope or by its changing directions. The software and hardware are initialized at step 250. Part of this initialization is to obtain an initial baseline value and a signal maximum and minimum. The signal baseline is continuously updated using a moving signal average with a window width of 2.5 seconds. The signal minimum and maximum is updated at every positive and negative peak where the absolute voltage change meets the programmed criteria. The signal is then analyzed at step 252 to determine if the signal direction is positive and above the baseline. If it is not, the signal is analyzed at step 254 to determine if it is negative and below the baseline. The system cycles between these two decision blocks until the criteria for one of the blocks is satisfied. However, this loop is limited by a max_curr_off timer applied to each of steps 252 and 254 which causes the system to restart at step 256 if it has been too long since the system was initialized or the last shock was terminated. The restart returns the system to step 250.

Once it has been determined at step 252 that a positive moving signal above the baseline has been detected, the signal is further analyzed at step 258 to determine if the slope of the signal is either below a preset maximum criteria or a direction change is detected. This essentially detects the top of a peak by looking for a near zero slope or a change of the sign of the slope. Additionally, a check is made of the peak to peak voltage of the signal based on stored maximum and minimum values to ensure that the signal is sufficiently large. This helps eliminate shocks at "glitches" which are not true peaks. If these criteria are not met, the system continues to check them until they are met or the max_curr_off timer times out and the system restarts at step 256. Once the criteria of step 258 are met, a check is made at step 260 to ensure that a minimum time has passed since the last shock was terminated. This prevents the system from getting locked in a loop delivering extremely rapid pulses. If this test of step 260 is met, the system stores the value of the signal for use with an autozero function and initiates the shock delivery to the heart at step 262. After the shock delivery is initiated, a successive approximation technique to put the input signal in range of the sensing system is started. A dead reckoning technique to correct the offset caused by the shock is used during the shock delivery. After a predetermined time, the pulse is terminated at step 264 and the baseline is restored by clearing the offset correction. At this point, the system would determine whether more pulses are called for as discussed above with reference to FIG. 4.

If it was determined at step 254 that a negative moving signal below the baseline was detected, the signal is further analyzed at step 266 to determine if the slope of the signal is either below a preset maximum criteria or a direction change is detected too. The check of the peak to peak voltage of the signal based on stored maximum and minimum values is also checked to ensure that the signal is sufficiently large. If these criteria are not met, the system continues to check them until they are met or the max_curr_off timer times out and the system restarts at step 256. If the criteria of step 266 are met, a check is made at step 268 to ensure that a minimum time has passed since the last shock was terminated. If this test of step 260 is met, the system stores the value of the signal for use with an autozero function and causes a negative shock to be delivered to the heart at step 270. After a predetermined time, the pulse is terminated at step 264 and the baseline is restored by the autozero function. At this point, the system would determine whether more pulses are called.

Figure 6A:
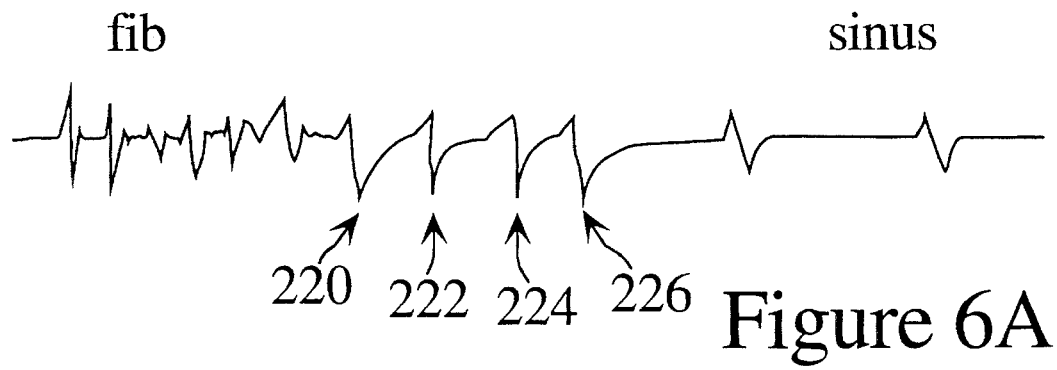
FIGS. 6A, 6B and 6C each provide a schematic representation of an electrogram illustrating a sequence of pulses delivered to the heart in accordance with an embodiment of the invention.
Figure 6B:
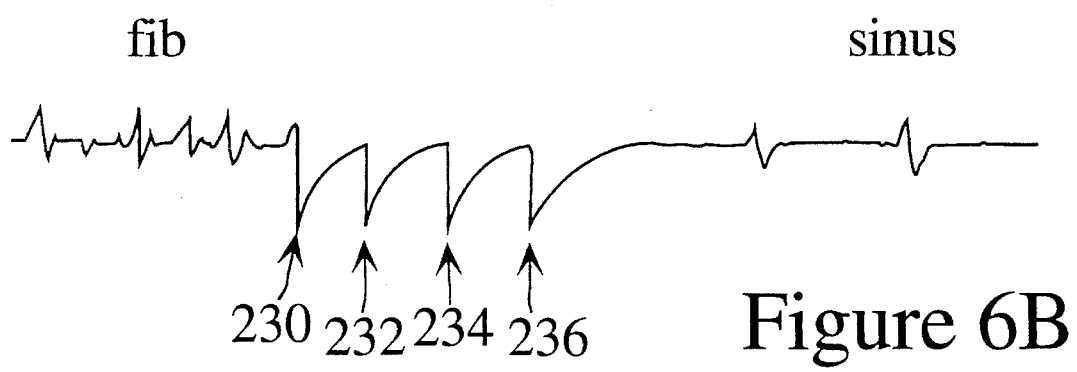
Figure 6C:
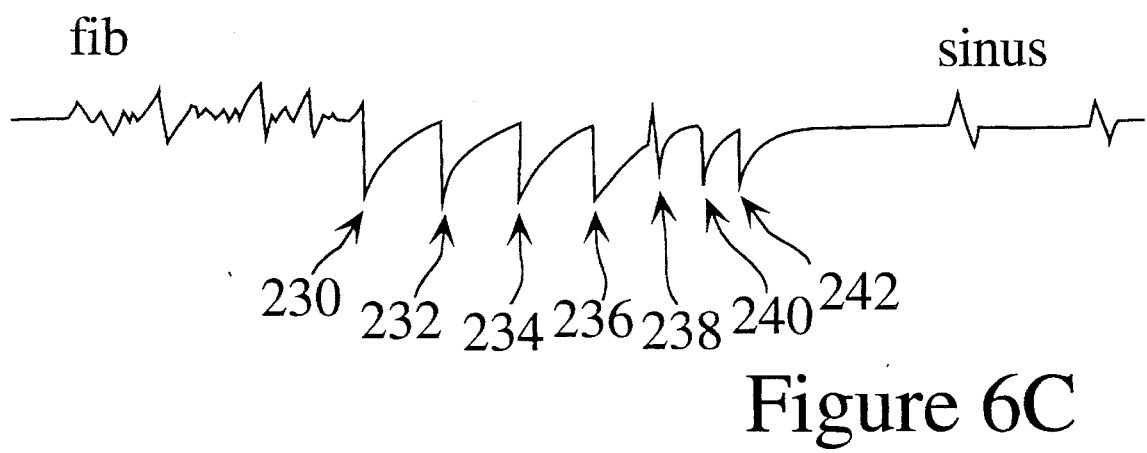

FIGS. 6A, 6B and 6C each provide a schematic representation of an electrogram illustrating a sequence of pulses delivered to the heart in accordance with an embodiment of the invention. It should be noted that the examples described above are illustrative only and do not represent actual therapy delivery with a human patient. In FIG. 6A, a fibrillation is detected and a series of four synchronous shocks 220, 222, 224 and 226 is delivered to the heart. The shocks are then ceased and, in the illustrated example, the heart is returned to a sinus condition. In this example, the synchronization trigger is generated based on a sensed peak or upstroke as the feature. The peak trigger can preferably be done by setting a predetermined amplitude threshold and triggering on a threshold crossing.

In the example of FIG. 6B, a first shock 230 is delivered synchronous with the peak or up stroke of the ECG in the fib signal. Following this first shock 230, a series of three shocks 232, 234 and 236 is delivered with each shock synchronized to a sensed return to baseline of the electrogram. The synchronization trigger is determined by detection of the feature of a low slope (dv/dt). In the example, the heart returns to a sinus rhythm following delivery of the synchronized shocks.

In the example shown in FIG. 6C, a first sequence of shocks is delivered as described with respect to FIG. 6B. The system then waits for the detection of a native complex 238. If one is detected within an interval representing a tachyarrhythmia following shock 236, then a shock 240 is delivered at 120 milliseconds following the native complex 238 and a shock 242 is delivered at 180 milliseconds following the native complex 238. The electrogram is shown returning to a sinus rhythm.

It should be understood that various alternatives to the embodiments of the invention described herein may be employed in practicing the invention. It is thus intended that the following claims define the scope of the invention and that structures and methods within the scope of these claims and their equivalents be covered thereby.

What is claimed is:

1. A method for treating a cardiac tachyarrhythmia in a patient's heart comprising:
    (a) sensing an EGG signal from said patient's heart to provide a sensed ECG signal, said sensed ECG signal including a series of sensed cardiac features;
    (b) detecting tachyarrhythmia; and
    (c) delivering in sequence a plurality of electrical pulses to said patient's heart, wherein at least two of said pulses being delivered are synchronous with at least two of said sensed cardiac features and wherein said sequence of electrical pulses is delivered before a determination is made as to whether said tachyarrhythmia has been terminated.

2. The method of claim 1 wherein said step of delivering includes delivering one of said plurality of electrical pulses for each one of a sequence of said series of sensed cardiac features.

3. The method of claim 1 and including the step of triggering the delivery of said electrical pulses based on an amplitude of said sensed ECG signal.

4. The method of claim 1 and including the step of triggering the delivery of said electrical pulses based on a rate of change of amplitude of said sensed ECG signal with respect to time.

5. The method of claim 1 and including the step of triggering the delivery of at least one of said electrical pulses based on an amplitude of said sensed ECG signal and at least one of said electrical pulses based on a rate of change of amplitude of said sensed ECG signal with respect to time.

6. The method of claim 1 wherein the delivery of one or more of said plurality of electrical pulses is delayed in time from a trigger signal.

7. The method of claim 1 wherein said step of delivering a plurality of electrical pulses includes delivering two or more synchronous pulses followed by one or more extra pulses spaced from a last one of said synchronous pulses by a predetermined interval.

8. The method of claim 1 wherein a first pulse of said plurality of pulses is delivered synchronous with a sensed cardiac feature having an amplitude greater than a threshold set as a function of the amplitude of a preceding series of sensed cardiac complexes.

9. The method of claim 1 and further including the step of monitoring a fibrillation interval and delivering a first pulse of said plurality of pulses based on a monitored regularity of said fibrillation interval.

10. The method of claim 1 wherein said step of detecting includes identifying cardiac complexes within said sensed ECG signal and measuring a plurality of intervals between a sequence of said cardiac complexes to characterize said tachyarrhythmia.

11. The method of claim 10 wherein said step of detecting further includes the step of averaging said plurality of intervals to characterize said tachyarrhythmia.

12. The method of claim 1 wherein said step of delivering includes delivering each of said electrical pulses as a waveform selected from the group consisting of monophasic, biphasic and multiphasic waveforms.

13. The method of claim 1 and further including the step of charging a capacitor prior to delivery of each of said electrical pulses and electrically coupling said capacitor to said patient's heart to deliver each of said electrical pulses.

14. The method of claim 1 wherein each of said electrical pulses has an amplitude, said method further including the step of modifying the amplitude of each subsequent pulse in said plurality of pulses relative to the amplitude of the preceding pulse.

15. The method of claim 1 wherein each of said electrical pulses has a duration, said method further including the step of modifying the duration of each subsequent pulse in said plurality of pulses relative to the duration of the preceding pulse.

16. The method of claim 1 wherein each of said electrical pulses has a duration and an amplitude, said method further including the step of modifying the amplitude and duration of each subsequent pulse in said plurality of pulses relative to the amplitude and duration of the preceding pulse.

17. The method of claim 1 wherein said step of delivering includes delivering each of said electrical pulses for a predetermined duration.

18. The method of claim 1 and further including the step of delivering one or more additional sequences of electrical pulses to said patient's heart.

19. The method of claim 18 and including the step of detecting the continued presence of an arrhythmia following delivery of a first or subsequent sequence of electrical pulses and delivering said one or more additional sequences of electrical pulses with an amplitude changed from the amplitude of a preceding sequence if said first or subsequent sequence fails to terminate said arrhythmia.

20. The method of claim 18 wherein the number of electrical pulses in one or more of said additional sequences is changed from the preceding sequence if a preceding sequence fails to terminate said arrhythmia.

21. A medical device for electrically stimulating a patient's heart comprising:

a sensing lead for sensing ECG signals of said patient's heart, said ECG signals including a series of cardiac features;

an ECG signal analyzer for detecting a tachyarrhythmia; and pulse delivery circuitry coupled to said signal analyzer and for delivering a plurality of electrical pulses to said patient's heart such that at least two of said electrical pulses are delivered synchronous with at least two of said cardiac features before a reduction is made of a possible tachyarrhythmia.

22. A medical device according to claim 21 wherein said ECG signal analyzer includes a microprocessor.

23. A medical device according to claim 21 wherein said pulse delivery circuitry includes a battery, a power supply circuit coupled to said battery and an output stage coupled to said power supply circuit.

24. A medical device for electrically stimulating a patient's heart comprising:

a sensor for sensing electrical signals of said patient's heart, said sensed signals including a sequence of sensed cardiac features;

a pulse generator adapted to generate a sequence of pulses wherein at least two of said pulses are synchronous with at least two of said cardiac features; and delivery means coupled to said pulse generator for delivering said pulses to said patient's heart after a first sensed tachyarrhythmia and prior to a next sensed tachyarrhythmia.

25. The medical device of claim 24 wherein said delivery means includes a pulse output stage and at least first and second electrodes coupled to said pulse output stage.

26. The medical device of claim 25 wherein said pulse generator includes circuitry for developing a synchronization trigger signal and a microprocessor coupled to said pulse output stage to control the delivery of said pulses upon receiving said trigger signal.

27. An implantable medical device for the electrical termination of tachyarrhythmia comprising:

sensing means responsive to cardiac depolarizations for producing a sense signal indicative of naturally occurring cardiac activity;

detection means responsive to said sensing means for detecting cardiac tachyarrhythmia and for producing a tachyarrhythmia signal indicative of such tachyarrhythmia;

trigger signal generating means responsive to said detection means for generating a trigger signal concurrent with each of said cardiac depolarizations; and pulse generator means responsive to said trigger signals for delivering a sequence of synchronous electrical pulses to cardiac tissue in response to said trigger signals.

28. The medical device of claim 27 wherein said pulse generator means includes a battery, at least one capacitor and a power supply circuit for charging said capacitor from said battery.

29. A method for treating a cardiac tachyarrhythmia in a patient's heart comprising:

(a) sensing an ECG signal from said patient's heart, said ECG signal including a series of cardiac features;

(b) detecting a tachyarrhythmia; and (c) delivering in sequence three or more electrical pulses to said patient's heart, at least two of said pulses being delivered synchronous with at least two of said cardiac features and wherein said sequence of electrical pulses is delivered before a determination is made as to whether said tachyarrhythmia has been terminated.

* * * * *

UNITED STATES PATENT AND TRADEMARK OFFICE
CERTIFICATE OF CORRECTION

PATENT NO. : 5,489,293
DATED : Feb. 6, 1996
INVENTOR(S) : Benjamin D. Pless, et al It is certified that error appears in the above-indentified patent and that said Letters Patent is hereby corrected as shown below:

Col. 14, Claim 21, Line 29 "before a reduction is made" should be "before a redetection is made"

Signed and Sealed this

Twenty-first Day of May, 1996

Attest:

BRUCE LEHMAN

Attesting Officer

Commissioner of Patents and Trademarks